(12) United States Patent
Liebing

(10) Patent No.: US 9,759,237 B2
(45) Date of Patent: *Sep. 12, 2017

(54) PUMP ARRANGEMENT

(71) Applicant: ECP ENTWICKLUNGSGESELLSCHAFT MBH, Berlin (DE)

(72) Inventor: Reiner Liebing, Berlin (DE)

(73) Assignee: ECP ENTWICKLUNGSGESELLSCHAFT MBH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/142,835

(22) Filed: Apr. 29, 2016

(65) Prior Publication Data

US 2016/0319846 A1    Nov. 3, 2016

Related U.S. Application Data

(63) Continuation of application No. 13/261,515, filed as application No. PCT/EP2011/002522 on May 16, 2011, now Pat. No. 9,328,741.

(Continued)

(30) Foreign Application Priority Data

May 17, 2010    (EP) .................................... 10075202

(51) Int. Cl.
*A61M 1/10*    (2006.01)
*F04F 5/10*    (2006.01)
(Continued)

(52) U.S. Cl.
CPC .............. *F04F 5/10* (2013.01); *A61M 1/101* (2013.01); *A61M 1/1008* (2014.02);
(Continued)

(58) Field of Classification Search
CPC .. A61M 1/101; A61M 1/1024; A61M 1/1084; A61M 1/125; A61M 1/1034
(Continued)

(56) References Cited

U.S. PATENT DOCUMENTS 2,350,534 A    6/1944  Rosinger
3,333,127 A    7/1967  Congdon et al.
(Continued)

FOREIGN PATENT DOCUMENTS

CA    1008330 A      4/1977
CA    2311977 A1    12/2000
(Continued)

OTHER PUBLICATIONS

Brochure Impella Pumpsystem of Impella CardioSystems AG, "Turning Lives Around," Aug. 2003 (4 pages).
(Continued)

*Primary Examiner* — Alyssa M Alter
(74) *Attorney, Agent, or Firm* — White & Case LLP

(57) ABSTRACT

The subject matter of the present invention is a pump arrangement (1, 10, 20, 30, 40, 50), in particular for use in the body's own vessels, having a pump (11, 41, 51) and a sheath (12, 42, 52) receiving the pump, bounding a flow passage (S) and having a distal intake opening (13, 43, 53) and a proximal outflow opening (14, 29, 39, 44, 54) for producing a driving flow by means of the pump, wherein the pump is arranged in a first fluid-tight section (12a, 42a, 52a) having the distal intake opening and a second fluid-tight section (12b, 42b, 52b) includes the proximal outflow opening. In accordance with the invention, a further inlet opening (15) is present between the first section and the second section and is arranged between the intake opening and the outflow opening, with the first section and the second section (Continued)

Figure 1:
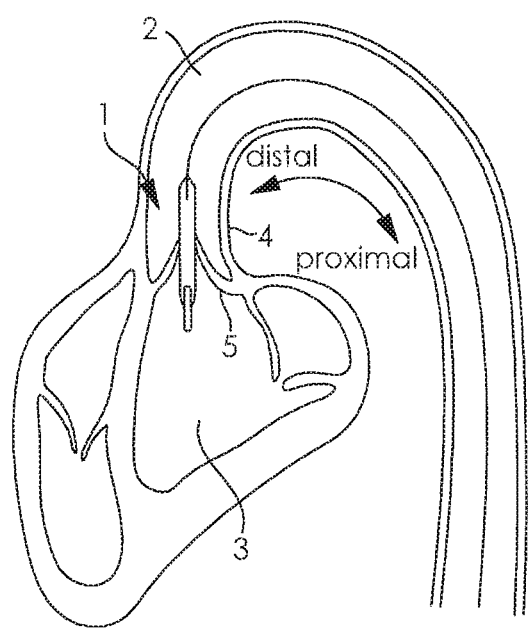

being arranged with respect to one another such that the inlet opening opens into the flow proximal to the pump.

20 Claims, 5 Drawing Sheets

Related U.S. Application Data

(60) Provisional application No. 61/345,253, filed on May 17, 2010.

(51) Int. Cl.
- *A61M 1/12* (2006.01)
- *F04D 3/00* (2006.01)
- *F04D 7/00* (2006.01)
- *F04D 29/02* (2006.01)
- *F04D 29/18* (2006.01)
- *F04D 29/52* (2006.01)

(52) U.S. Cl.
CPC ........ *A61M 1/1024* (2014.02); *A61M 1/1034* (2014.02); *A61M 1/1084* (2014.02); *A61M 1/125* (2014.02); *F04D 3/00* (2013.01); *F04D 7/00* (2013.01); *F04D 29/026* (2013.01); *F04D 29/181* (2013.01); *F04D 29/528* (2013.01)

(58) Field of Classification Search
USPC ...................................................... 264/328.1
See application file for complete search history.

(56) References Cited

U.S. PATENT DOCUMENTS

| | | |
|---|---|---|
| 3,354,833 A | 11/1967 | Laing |
| 3,489,145 A | 1/1970 | Judson et al. |
| 3,501,229 A | 3/1970 | Smith |
| 3,568,659 A | 3/1971 | Karnegis |
| 3,802,551 A | 4/1974 | Somers |
| 3,812,812 A | 5/1974 | Hurwitz |
| 3,936,683 A | 2/1976 | Walker |
| 4,014,317 A | 3/1977 | Bruno |
| 4,065,234 A | 12/1977 | Yoshiyuki et al. |
| 4,115,040 A | 9/1978 | Knorr |
| 4,135,253 A | 1/1979 | Reich et al. |
| 4,153,048 A | 5/1979 | Magrini |
| 4,207,028 A | 6/1980 | Ridder |
| 4,420,851 A | 12/1983 | Wiener |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,728,319 A | 3/1988 | Masch |
| 4,747,821 A | 5/1988 | Kensey et al. |
| 4,747,840 A | 5/1988 | Ladika et al. |
| 4,749,376 A | 6/1988 | Kensey et al. |
| 4,753,221 A | 6/1988 | Kensey et al. |
| 4,777,951 A | 10/1988 | Cribier |
| 4,801,243 A | 1/1989 | Norton |
| 4,817,613 A | 4/1989 | Jaraczewski et al. |
| 4,846,152 A | 7/1989 | Wampler et al. |
| 4,895,557 A | 1/1990 | Moise et al. |
| 4,919,647 A | 4/1990 | Nash |
| 4,957,504 A | 9/1990 | Chardack |
| 4,964,864 A | 10/1990 | Summers et al. |
| 4,969,865 A | 11/1990 | Hwang et al. |
| 4,984,972 A | 1/1991 | Clausen et al. |
| 4,995,857 A | 2/1991 | Arnold |
| 5,011,469 A | 4/1991 | Buckberg et al. |
| 5,017,103 A | 5/1991 | Dahl |
| 5,037,403 A | 8/1991 | Garcia |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,112,349 A | 5/1992 | Summers et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,147,186 A | 9/1992 | Buckholtz |
| 5,158,279 A | 10/1992 | Laffey et al. |
| 5,163,431 A | 11/1992 | Griep |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,250,059 A | 10/1993 | Andreas et al. |
| 5,275,580 A | 1/1994 | Yamazaki |
| 5,300,112 A | 4/1994 | Barr |
| 5,357,963 A | 10/1994 | Mayol et al. |
| 5,373,619 A | 12/1994 | Fleischhacker et al. |
| 5,376,114 A | 12/1994 | Jarvik |
| 5,405,383 A | 4/1995 | Barr |
| 5,421,338 A | 6/1995 | Crowley et al. |
| 5,480,392 A | 1/1996 | Mous |
| 5,501,574 A | 3/1996 | Raible |
| 5,531,789 A | 7/1996 | Yamazaki et al. |
| 5,701,911 A | 12/1997 | Sasamine et al. |
| 5,749,855 A | 5/1998 | Reitan |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,827,171 A | 10/1998 | Dobak, III et al. |
| 5,851,174 A | 12/1998 | Jarvik et al. |
| 5,863,179 A | 1/1999 | Westphal et al. |
| 5,882,329 A | 3/1999 | Patterson et al. |
| 5,888,241 A | 3/1999 | Jarvik |
| 5,911,685 A | 6/1999 | Siess et al. |
| 5,938,672 A | 8/1999 | Nash |
| 5,954,745 A | 9/1999 | Gertler et al. |
| 5,964,694 A | 10/1999 | Siess et al. |
| 6,001,078 A | 12/1999 | Reekers |
| 6,030,397 A | 2/2000 | Monetti et al. |
| 6,054,788 A | 4/2000 | Dombrovski et al. |
| 6,058,593 A | 5/2000 | Siess |
| 6,083,260 A | 7/2000 | Aboul-Hosn |
| 6,123,725 A | 9/2000 | Aboul-Hosn |
| 6,129,704 A | 10/2000 | Forman et al. |
| 6,139,487 A | 10/2000 | Siess |
| 6,152,693 A | 11/2000 | Olsen et al. |
| 6,168,624 B1 | 1/2001 | Sudai |
| 6,183,220 B1 | 2/2001 | Ohara et al. |
| 6,245,007 B1 | 6/2001 | Bedingham et al. |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,413,222 B1 | 7/2002 | Pantages et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,517,528 B1 | 2/2003 | Pantages et al. |
| 6,527,521 B2 | 3/2003 | Noda |
| 6,533,716 B1 | 3/2003 | Schmitz-Rode et al. |
| 6,537,030 B1 | 3/2003 | Garrison |
| 6,537,247 B2 | 3/2003 | Shannon |
| 6,537,315 B2 | 3/2003 | Yamazaki et al. |
| 6,544,216 B1 | 4/2003 | Sammler et al. |
| 6,592,612 B1 | 7/2003 | Samson et al. |
| 6,652,548 B2 | 11/2003 | Evans et al. |
| 6,719,791 B1 | 4/2004 | Nusser et al. |
| 6,790,171 B1 | 9/2004 | Grundeman et al. |

(56) References Cited

U.S. PATENT DOCUMENTS

| | | |
|---|---|---|
| 6,841,910 B2 | 1/2005 | Gery |
| 6,858,001 B1 | 2/2005 | Aboul-Hosn |
| 6,860,713 B2 | 3/2005 | Hoover |
| 6,942,672 B2 | 9/2005 | Heilman et al. |
| 6,945,977 B2 | 9/2005 | Demarais et al. |
| 6,974,436 B1 | 12/2005 | Aboul-Hosn et al. |
| 6,976,996 B1 | 12/2005 | Aboul-Hosn |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,646,376 B2 | 1/2010 | Blersch |
| 7,731,675 B2 | 6/2010 | Aboul-Hosn et al. |
| 7,841,976 B2 | 11/2010 | McBride et al. |
| 7,927,068 B2 | 4/2011 | McBride et al. |
| 7,934,909 B2 | 5/2011 | Nuesser et al. |
| 8,439,859 B2 | 5/2013 | Pfeffer et al. |
| 8,888,728 B2 | 11/2014 | Aboul-Hosn et al. |
| 9,328,741 B2 * | 5/2016 | Liebing ................. A61M 1/101 |
| 2001/0000528 A1 | 4/2001 | Cho |
| 2002/0123661 A1 | 9/2002 | Verkerke et al. |
| 2002/0151799 A1 | 10/2002 | Pantages et al. |
| 2003/0135086 A1 | 7/2003 | Khaw et al. |
| 2003/0135940 A1 | 7/2003 | Lev et al. |
| 2003/0208097 A1 | 11/2003 | Aboul-Hosn et al. |
| 2003/0231959 A1 | 12/2003 | Snider |
| 2004/0022640 A1 | 2/2004 | Siess et al. |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0113502 A1 | 6/2004 | Li et al. |
| 2004/0193046 A1 | 9/2004 | Nash et al. |
| 2004/0215222 A1 | 10/2004 | krivoruchko |
| 2004/0215228 A1 | 10/2004 | Simpson et al. |
| 2004/0260237 A1 | 12/2004 | Squadrito |
| 2005/0135942 A1 | 6/2005 | Wood et al. |
| 2006/0008349 A1 | 1/2006 | Khaw |
| 2006/0062672 A1 | 3/2006 | McBride et al. |
| 2006/0195004 A1 | 8/2006 | Jarvik |
| 2007/0118072 A1 | 5/2007 | Nash |
| 2008/0103591 A1 | 5/2008 | Siess |
| 2008/0114339 A1 | 5/2008 | McBride et al. |
| 2008/0132747 A1 | 6/2008 | Shifflette |
| 2008/0132748 A1 | 6/2008 | Shifflette |
| 2008/0183136 A1 | 7/2008 | Lenker et al. |
| 2008/0262584 A1 | 10/2008 | Bottomley et al. |
| 2008/0306327 A1 | 12/2008 | Shifflette |
| 2009/0060743 A1 | 3/2009 | McBride et al. |
| 2009/0062597 A1 | 3/2009 | Shifflette |
| 2009/0088609 A1 | 4/2009 | Schmitz-Rode et al. |
| 2009/0093764 A1 | 4/2009 | Pfeffer et al. |
| 2009/0093796 A1 | 4/2009 | Pfeffer et al. |
| 2009/0218728 A1 | 9/2009 | Moyer |
| 2009/0227892 A1 | 9/2009 | Krombach et al. |
| 2010/0041939 A1 | 2/2010 | Siess |
| 2010/0210895 A1 | 8/2010 | Aboul-Hosn et al. |
| 2010/0268017 A1 | 10/2010 | Siess |
| 2011/0071338 A1 | 3/2011 | McBride et al. |
| 2011/0238172 A1 | 9/2011 | Akdis |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0184803 A1 | 7/2012 | Simon et al. |
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0066140 A1 | 3/2013 | McBride et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |
| 2015/0073202 A1 | 3/2015 | Aboul-Hosn et al. |

FOREIGN PATENT DOCUMENTS

| | | |
|---|---|---|
| CA | 2613175 A1 | 1/2007 |
| CA | 2632420 A1 | 6/2007 |
| CA | 2701809 A1 | 4/2009 |
| CA | 2701810 A1 | 4/2009 |
| DE | 2207296 A1 | 8/1972 |
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 4414903 A1 | 11/1995 |
| DE | 69017784 T2 | 11/1995 |
| DE | 19535781 A1 | 3/1997 |
| DE | 19711935 A1 | 4/1998 |
| DE | 29804046 U1 | 4/1998 |
| DE | 69407869 T2 | 4/1998 |
| DE | 69427390 T2 | 9/2001 |
| DE | 100 59 714 C1 | 5/2002 |
| DE | 10108810 A1 | 8/2002 |
| DE | 10249371 A1 | 4/2003 |
| DE | 10155011 A1 | 5/2003 |
| DE | 69431204 T2 | 8/2003 |
| DE | 10336902 B3 | 8/2004 |
| DE | 102004054714 A1 | 5/2006 |
| DE | 102005039950 A1 | 3/2007 |
| DE | 102010011998 A1 | 9/2010 |
| EP | 0364293 A2 | 4/1990 |
| EP | 0445782 A1 | 9/1991 |
| EP | 0480102 A1 | 4/1992 |
| EP | 0560000 A2 | 9/1993 |
| EP | 0629412 A2 | 12/1994 |
| EP | 0764448 A2 | 3/1997 |
| EP | 0768091 A1 | 4/1997 |
| EP | 0768900 A1 | 4/1997 |
| EP | 0884064 A2 | 12/1998 |
| EP | 0914171 A2 | 5/1999 |
| EP | 0916359 A1 | 5/1999 |
| EP | 951302 A2 | 10/1999 |
| EP | 1019117 A1 | 7/2000 |
| EP | 1034808 A1 | 9/2000 |
| EP | 1066851 A1 | 1/2001 |
| EP | 1114648 A2 | 7/2001 |
| EP | 1207934 A2 | 5/2002 |
| EP | 1337288 A1 | 8/2003 |
| EP | 1651290 A1 | 5/2006 |
| EP | 2047872 A1 | 4/2009 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 2497521 A1 | 9/2012 |
| EP | 2606919 A1 | 6/2013 |
| EP | 2606920 A1 | 6/2013 |
| EP | 2607712 A1 | 6/2013 |
| FR | 2788223 A1 | 7/2000 |
| GB | 2239675 A | 7/1991 |
| JP | H04126158 A | 4/1992 |

(56) References Cited

FOREIGN PATENT DOCUMENTS

| | | |
|---|---|---|
| RU | 2229899 C2 | 6/2004 |
| WO | WO-9202263 A1 | 2/1992 |
| WO | WO-9302732 A1 | 2/1993 |
| WO | WO-9303786 A1 | 3/1993 |
| WO | WO-9314805 A1 | 8/1993 |
| WO | WO-9401148 A1 | 1/1994 |
| WO | WO-9405347 A1 | 3/1994 |
| WO | WO-9409835 A1 | 5/1994 |
| WO | WO-9420165 A2 | 9/1994 |
| WO | WO-9523000 A2 | 8/1995 |
| WO | WO-9618358 A1 | 6/1996 |
| WO | WO-9625969 A2 | 8/1996 |
| WO | WO-9744071 A1 | 11/1997 |
| WO | WO-9853864 A1 | 12/1998 |
| WO | WO-9919017 A1 | 4/1999 |
| WO | WO-9944651 A1 | 9/1999 |
| WO | WO-99/58170 A1 | 11/1999 |
| WO | WO-0019097 | 4/2000 |
| WO | WO-0027446 A1 | 5/2000 |
| WO | WO-0043053 | 7/2000 |
| WO | WO-0043054 A2 | 7/2000 |
| WO | WO-0062842 A1 | 10/2000 |
| WO | WO-0107760 | 2/2001 |
| WO | WO-0107787 | 2/2001 |
| WO | WO-0183016 | 11/2001 |
| WO | WO-0222200 | 3/2002 |
| WO | WO-0243791 | 6/2002 |
| WO | WO-03057013 | 7/2003 |
| WO | WO-03103745 | 12/2003 |
| WO | WO-2005002646 A1 | 1/2005 |
| WO | WO-2005016416 A1 | 2/2005 |
| WO | WO-2005021078 A1 | 3/2005 |
| WO | WO-2005030316 A1 | 4/2005 |
| WO | WO-2005032620 A1 | 4/2005 |
| WO | WO-2005081681 A2 | 9/2005 |
| WO | WO-2006020942 A1 | 2/2006 |
| WO | WO-2006034158 A2 | 3/2006 |
| WO | WO-2006133209 A1 | 12/2006 |
| WO | WO-2007003351 A1 | 1/2007 |
| WO | WO-2007103390 A2 | 9/2007 |
| WO | WO-2007103464 A2 | 9/2007 |
| WO | WO-2007112033 A2 | 10/2007 |
| WO | WO-2008017289 A2 | 2/2008 |
| WO | WO-2008034068 A2 | 3/2008 |
| WO | WO-2008054699 A2 | 5/2008 |
| WO | WO-2008106103 A2 | 9/2008 |
| WO | WO-2008116765 A2 | 10/2008 |
| WO | WO-2008124696 A1 | 10/2008 |
| WO | WO-2008137352 A1 | 11/2008 |
| WO | WO-2008137353 A1 | 11/2008 |
| WO | WO-2009015784 A1 | 2/2009 |
| WO | WO-2010063494 A1 | 6/2010 |
| WO | WO-2010127871 A1 | 11/2010 |
| WO | WO-2010133567 A1 | 11/2010 |
| WO | WO-2013034547 A1 | 3/2013 |
| WO | WO-2013092971 A1 | 6/2013 |
| WO | WO-2013093058 A1 | 6/2013 |
| WO | WO-2013093301 A1 | 6/2013 |

OTHER PUBLICATIONS

Buecker A et al., "Use of a Nonmetallic Guide Wire for Magnetic Resonance—Guided Coronary Artery Catheterization," Investigative Radiology, 39:11, pp. 656-660 (2004).
Compendium of Technical and Scientific Information for the Hemopump Temporary Cardiac Assist System, 1988 (15 pages).
Dekker, Andre, et al, "Efficacy of a New Intraaortic Propeller Pump vs the Intraaortic Balloon Pump," Chest Journal; Jun. 2003 (7 pages).
Frazier, O.H., et al, "First Human Use of the Hemopump, A Cather-Mounted Ventricular Assist Device," Ann Thorac Surg., Feb; 49(2): pp. 299-304 (1990).
International Preliminary Report on Patentability, from PCT/EP09/008858, issued Jun. 7, 2011 (5 pages).
Jomed Reitan Catheter Pump Brochure, www.jomed.com/rcp (undated) (6 pages).
Lueger, Lexikon der Technik, "Lexikon der Feinwerktechnik", vol. 13, Deutsche Verlags—Anstalt GmbH, Stuttgart, seite 551 (4 pages) (1968).
Reitan, Oyvind et al, "Hydrodynamic Properties of a New Percutaneous Intra-aortic Axial Flow Pump," ASAIO Journal; May-June; vol. 16; 6 pages (2000).
Rothman, Martin T, "The Reitan Catheter Pump: A New Versatile Approach for Hemodynamic Support," London Chest Hospital Barts & the Long NHS Trust, presented at TCT Conference, Oct. 24-26, 2006, (40 pages).
Schmitz-Rode, T et al., "An Expandable Percutaneous Catheter Pump for Left Ventricular Support," Journal of the American College of Cardiology, 45:11, pp. 1856-1861 (2005).
Schmitz-Rode, T et al, "Temporary Pulmonary Stent Placement as Emergency Treatment of Pulmonary Embolism," Journal of the American College of Cardiology, 48:4, pp. 812-816 (2006).
Siess, Thorsten, "Systemanalyse and Entwicklung intravasaler Rotationspumpen zur Herzunterstutzung," Helmholtz-Institut, Jun. 24, 1998 (105 pages) and partial English translation (39 pages).
Verma, R et al., "Evaluation of a Newly Developed Percutaneous Thrombectomy Basket Device in Sheep with Central Pulmonary Embolisms," Investigative Radiology, 41:10, pp. 729-734 (2006).
Wampler, Richard, K., "In Vivo Evaluation of a Peripheral Vascular Access Axial Flow Blood Pump," ASAIO Trans., Jul-Sep;34(3): pp. 450-454 (1988).

* cited by examiner

PUMP ARRANGEMENT

CROSS-REFERENCE TO RELATED APPLICATIONS

This application is a continuation of U.S. patent application Ser. No. 13/261,515, which entered the national stage on Nov. 13, 2012 and which is a United States National Stage filing under 35 U.S.C. §371 of International Application No. PCT/EP2011/002522, filed May 16, 2011, which claims the benefit of U.S. Provisional Patent Application No. 61/345,253, filed May 17, 2010, and European Patent Application No. 10075202.1, filed May 17, 2010, the contents of all of which are incorporated by reference herein in their entirety. International Application No. PCT/EP2011/002522 was published under PCT Article 21(2) in English.

The invention is in the field of mechanical engineering and fine mechanics and can in particular advantageously be used in the medical area.

In this respect, the subject matter is a pump arrangement in accordance with the preamble of claim 1.

Pump arrangements are increasingly known from prior art in particular for use in the body's own vessels. Said pumps can be used, for example, for short-term cardiac support to relieve the cardiac muscle of a patient after a cardiogenic shock (myocardial infarction). In this process, use is sometimes made of transfemorally implanted micro-axial pumps.

Such a pump arrangement is known, for example, from EP 2 047 872 A1. The pump arrangement disclosed there includes a pump, a sheath receiving the pump and having a distal intake opening and a proximal outflow opening, with the pump generating a driving flow in operation from the distal intake opening toward the proximal outflow opening. A flow passage thus extends between the intake opening and the outflow opening. The pump is in this respect arranged in a first fluid-tight section of the sheath which has the distal intake opening and which is formed as a PU covering of a housing. Furthermore, a second fluid-tight section of the sheath is present which includes the proximal outflow opening and is formed as an outflow hose. The outflow hose is connected with material continuity to the PU covering. The pump arrangement is arranged such that the pump formed as a rotor can, for example, be arranged in a ventricle, with the outflow hose extending from the ventricle into the aorta.

All the blood entering into the aorta via outflow openings of the outflow hose moves through the intake opening into the flow passage formed by the sheath and in so doing passes through the rotor. In other words: The conveyed flow conveyed by the pump is identical to the total flow exiting at the outflow opening.

The subject matters of documents DE 41 24 299 A1, DE 10 2004 054 714 A1, WO 2007/112033 A2 and US 2008/132748 A1 also work in accordance with the aforesaid principle.

Since all blood comes into direct contact with the pump, a particularly high effort is required in the manufacture of the pump to reduce the blood-damaging effect of the moving pump parts. This blood-damaging effect is manifested in direct mechanical shear at moving and stationary pump parts and in shear by shear stress fields occurring in the fluid while passing through the flow passage (see above). Pump geometries therefore also arise which cannot be used by means of a minimally invasive procedure.

It is the underlying object of the present invention to reduce the danger of damage to the blood or to the fluid transported through the pump. Special attention must be paid to the choice of the materials in the medical use of the following pump arrangement(s). Said materials should meaningfully satisfy the demands of biocompatibility. Interactions with foreign-body surfaces form the third big aspect, in addition to the above implementation, in blood damage and have been sufficiently examined for some time.

In accordance with the invention, a further inlet opening is introduced between the first section and the second section with the first section and the second section being arranged with respect to one another such that the inlet opening opens into the flow passage proximal the compressible pump. In this respect, the further inlet opening can also be formed as an inlet passage which has its inlet opening distal of or proximal to the pump or also at the level of the pump, but which only opens into the flow passage proximal to the pump.

It is possible with the aid of the feature in accordance with the invention that a driving flow running through the pump flows through the flow passage past the opening of the inlet opening in the direction of the outlet opening and thus effects a pressure drop with respect to the fluid pressure present in the inlet opening which results in a pulling of fluid through the inlet opening and into the flow passage. The total flow outflowing at the outflow opening is hereby larger than the driving flow directly passing through the pump and conveyed thereby since an additional intake flow is added through the inlet flow.

The intake flow arises in that a suction effect arises due to the driving flow such as also occurs in some kinds of turbine or water jet pumps. On the suction effect, an impulse is transmitted from the driving flow to the intake flow by friction or viscosity or turbulent mixing of the fluid. In this manner, viscous, turbulent shear stresses arise. The impulse direction of the propellant flow is transmitted to particles from the medium of the intake flow to be conveyed which are transported into a zone downstream within the sheath.

Substantially, the principle of a jet pump is realized with the aid of the feature in accordance with the invention, with the driving flow directly passing through the pump and conveyed thereby carrying along an intake flow entering through the further inlet opening.

The inlet opening in this respect extends between the first section and the second section, with the entry to the inlet opening being able to be proximal to or distal of the pump, with it being advantageous if the entry is distal of the outflow opening. Only the opening of the inlet opening into the flow passage should be proximal the pump so that the suction effect which is caused by the driving flow is utilized well.

A compressible pump is understood as a preferably radially compressible pump or pump arrangement. In this respect, the pump or the first section and/or the second section and/or the housing and/or the rotor are formed such that the pump can be conducted to the target site in a catheter, with the catheter having an inner diameter which is smaller than the first section and second section or the housing in the unfolded condition. Such pumps or pump arrangements are known, for example, in EP 2 047 872 A1, in WO 2010/063494 A1, in U.S. 61/120,095 or in WO 2010/127871 and in U.S. 61/175,519 A1.

An inlet opening formed between the intake opening and the outflow opening is particularly advantageous.

The first section and the second section of the sheath can be formed in one piece or as components separate from one another.

In a first embodiment, the cross-section of the proximal end of the first section is smaller than the cross-section of the distal end of the second section. The conveyed flow is hereby concentrated onto an area of the cross-section of the proximal end of the first section and can take along further medium on entry into the second section, said medium being able to flow in at least through accesses in the region of the remaining area of the cross-section of the distal end of the second section.

In a further embodiment, the cross-section of the first section converges toward its proximal end. Due to this convergence, the first section is of nozzle form at its proximal end. This results in an improvement in the efficiency and thus in an increase in the sucked-in intake flow. In addition, the feature helps effect a reduction in the total pump arrangement.

In a further embodiment, the distal end of the second section and the proximal end of the first section overlap, i.e. the distal end of the second section is further distal than the proximal end of the first section. In this respect, it is advantageous if the inlet opening between the first section and the second section is in each case formed as an intake passage or in the manner of a passage from the distal end of the second section toward the proximal end of the first section. The intake flow hereby preferably flows almost coaxially to the conveyed direction of the driving flow through the intake passage into the flow passage in the direction of the outflow opening. In this respect, an impulse of the driving flow in the direction of the outflow opening is already transmitted to the intake flow due to the main axis of the intake passage which is preferably directed in the direction of the conveyed flow. This results in an improvement in efficiency.

In a further embodiment, the distal end of the second section is further proximal than or at the same level as the proximal end of the first section. Due to the spacing, the concentrated driving flow exiting the proximal end of the first section is incident onto a fluid of different pressure and different directions so that the concentrated conveyed flow, like a fluid of higher density, flows on into the start of the second section defined by the distal end of the second section and takes along fluid which is located between the first section and the second section. The total flow hereby becomes larger with respect to the driving flow passing through the pump. In this respect, care must, however, be taken that the spacing between the distal end of the second section and the proximal end of the first section is kept small in order not to effect any dispersion of the conveyed flow with respect to the flow present outside the sheath. The spacing should be approximately from 0 to ¼ of the diameter of the proximal outlet opening of the first section.

In a further embodiment, the second section includes at least one partial region made from a flexible material. It is hereby possible that a second section which is disposed between, for example, a ventricle and a blood vessel, with the ventricle and the blood vessel being connected by means of a valve closing and opening rhythmically, can be pressed through the valve and the fluid is thus conveyed in turn with the rhythmic movement of the valve. PU, PE, PP, silicone or Parylene are, for example suited as suitable materials provided that they satisfy the mechanical and geometrical demands and the demands on biocompatibility.

In a further embodiment, the pump arrangement has a housing receiving the pump. This is in particular suitable when the pump is a compressible pump which is conveyed to its working site by means of a catheter together with the housing. In addition, the housing gives the pump arrangement additional stability. The housing can, for example, be manufactured from Nitinol.

On the presence of a housing, the first section can be made as a jacket of the housing or as a coating of the housing, with only a partial region of the housing, preferably an axial partial region, having to have a fluid-tight jacketing or coating.

Materials are suitable as coatings or jacketings here such as were already named in the description of the second section made from a flexible material.

In a further embodiment, the housing has a constriction and/or a bulge proximal to the pump. In this respect, a constriction is to be understood as a convergence of the cross-section of the housing with respect to the region of housing receiving the pump. A bulge has a cross-section of the housing enlarged with respect to a constriction or with respect to the region receiving the pump. Converging portions of the first section or lager cross-sections of the second section can be implemented in a particularly easy and advantageous manner with the aid of such a shape. The second section can also be connected to the housing.

In a further embodiment, the first section and the second section are connected to one another with material continuity or are preferably formed in one piece.

In a further embodiment, the second section is formed as an outflow hose.

In a further embodiment, the first section, the second section or any housing includes support elements such as a support ring, plastic threads, wires, connecting struts or a preferably compressible sleeve for spacing apart the first section and the second section so that an intake flow flowing through the inlet opening does not have the result that a surface of the second section is sucked onto the surface of the first section and thus interrupts the intake flow or to ensure that the further inlet opening is permanently open in pump operation. The support elements are in this respect connected to the first section or to the second section such that they are compressible together with the pump. This can be achieved, for example, via flexible support elements or support elements made from hyper elastic materials or support elements made from memory materials such as Nitinol.

The second section can furthermore have a support ring in the region of the inlet opening, said support ring ensuring a spacing of the first section from the second section in the region of the inlet opening so that an intake flow flowing through the inlet opening does not have the result that a surface of the second section is sucked onto the surface of the first section and thus interrupts the intake flow. This is in particular advantageous when the second section is a section made from flexible material such as an outflow hose.

In a further embodiment, the second section has a sleeve which includes the further inlet apparatus or partly includes the further inlet opening. Said sleeve can be connected as an additional special part, for example, to a flexible region of the second section. In this respect, it is advantageous if the sleeve is of stable shape and thus forms a suitable resistance with respect to the fluid in the working state which is defined, for example, by an unfolding of the pump arrangement at its work site in the body so that the intake flow is channeled by the sleeve and flows into the flow passage.

Instead of a sleeve, a further hose section or a tube can also be used.

In a further embodiment, the pump is a compressible pump, which results in a lighter introduction of the pump into the bloodstream or into a vessel.

It is furthermore advantageous if the pump is an axial flow pump which is fastened on a rotatable shaft which drives the pump.

Figure 2:
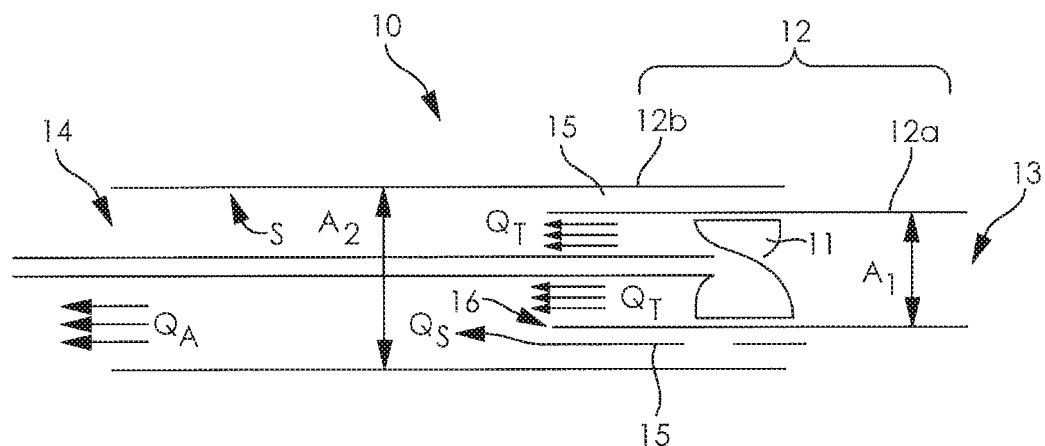
Figure 3:
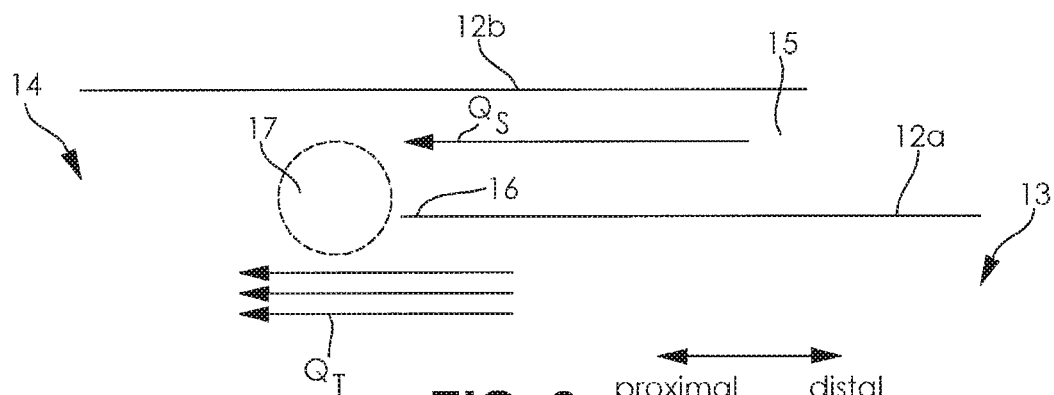
Figure 4:
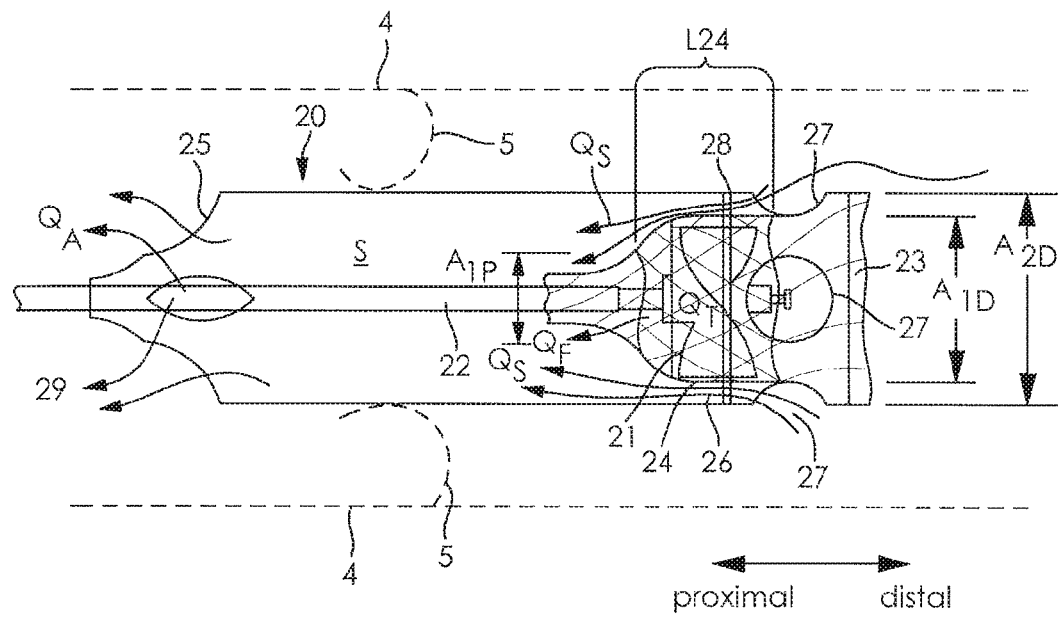
Figure 5A:
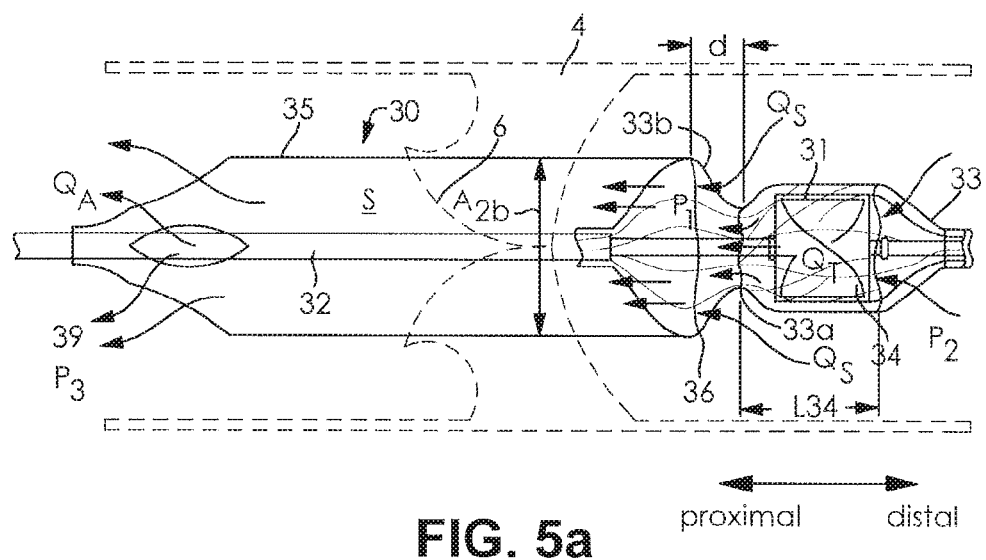
Figure 5B:
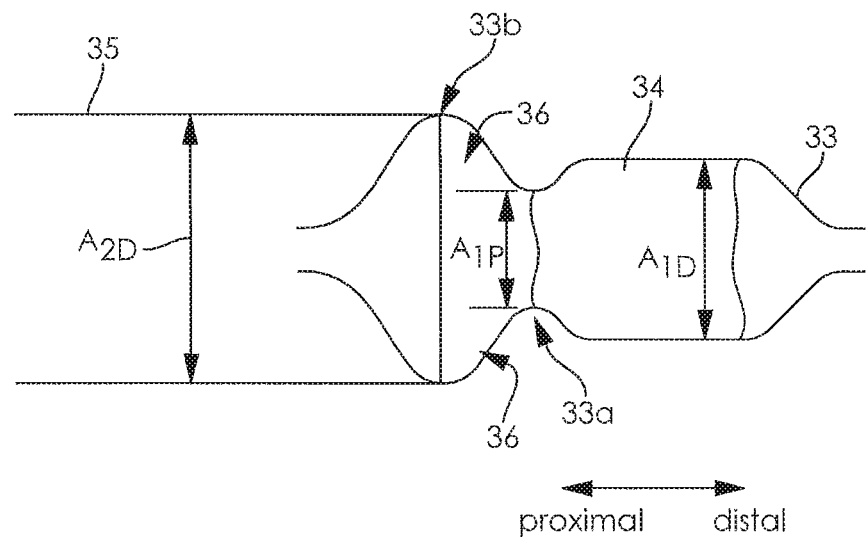
Figure 6:
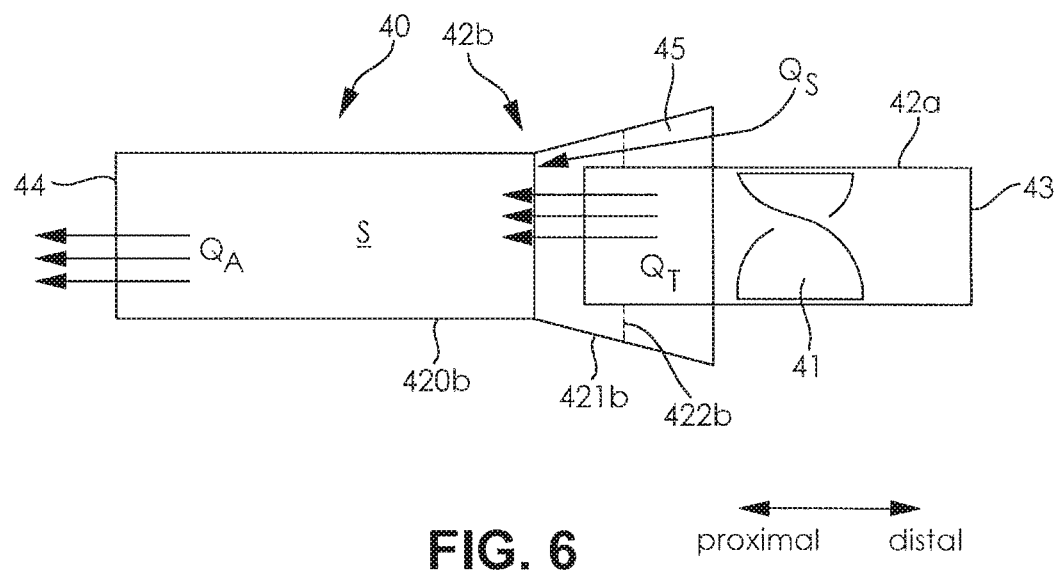
Figure 7:
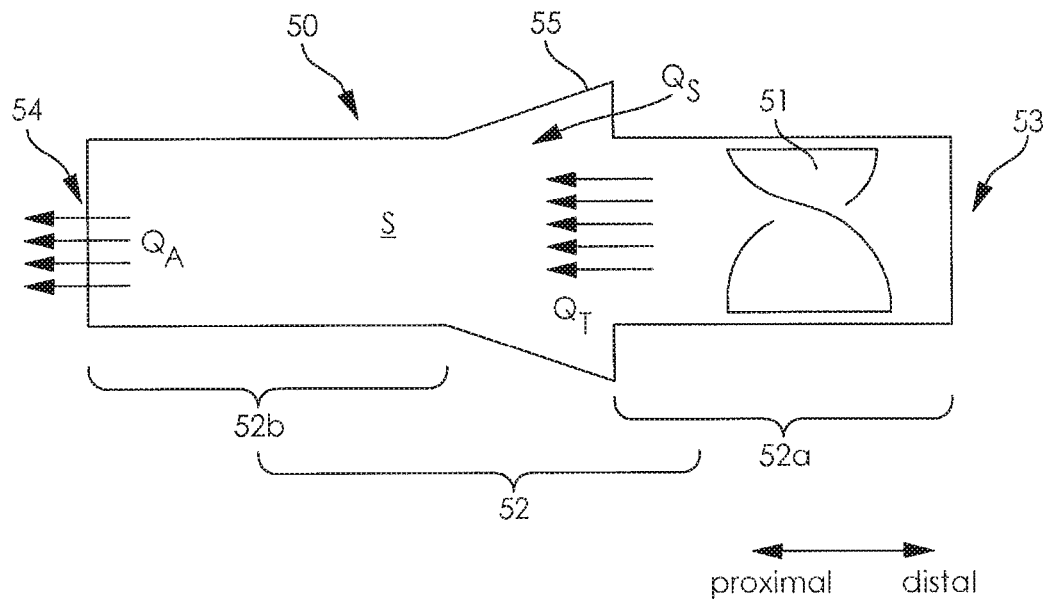

The invention will be described in the following in more detail with reference to some embodiments. There are shown:

FIG. 1 the use of a pump arrangement in a heart;

FIG. 2 a schematic representation of an embodiment of the pump arrangement;

FIG. 3 a schematic representation of an inlet opening of an embodiment of the pump arrangement;

FIG. 4 an embodiment of a pump arrangement;

FIG. 5a a further embodiment of a pump arrangement;

FIG. 5b a schematic representation of the pump arrangement of FIG. 5a;

FIG. 6 a further embodiment of a pump arrangement;

FIG. 7 a further embodiment of a pump arrangement; and

Figure 8A:
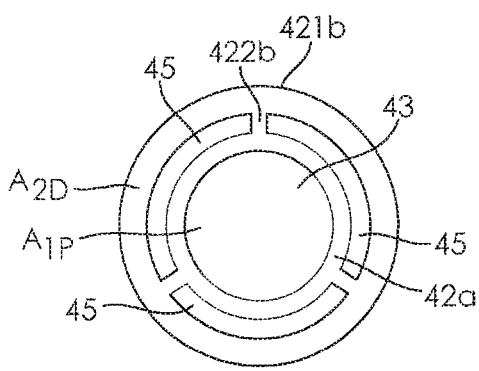
Figure 8B:
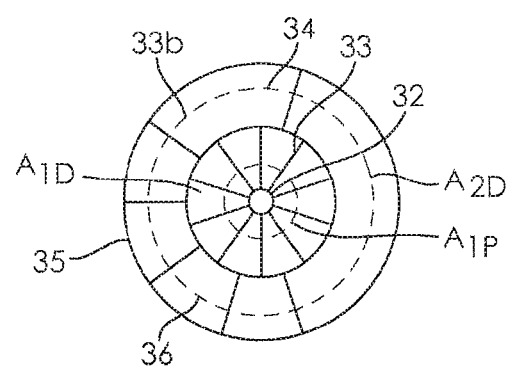
Figure 8C:
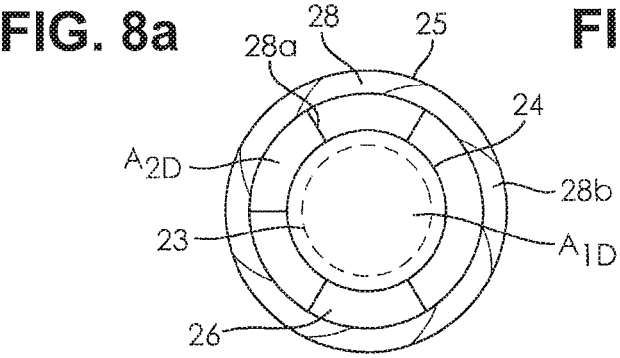

FIGS. 8a-8c cross-sections through different pump arrangements.

A possible use for the pump arrangement 1 is shown in FIG. 1. The pump arrangement 1 includes an elongate catheter which extends through the blood vessel 2 and in which a shaft extends which drives the pump present in the pump arrangement 1 and formed as a rotor. The proximal end of the pump arrangement (viewed without the catheter) is located in the blood vessel 2, whereas the distal end of the pump arrangement 1 including the pump is located in the ventricle 3. The blood vessel 2 is bounded by the vessel wall 4. The valve 5 which opens and closes rhythmically furthermore bounds the ventricle 3 and enables the blood flow from the ventricle 3 into the blood vessel 2.

Further uses are possible in addition to the shown use of a pump arrangement in accordance with the information. The pump can thus, for example, be used in a different vessel of the body to increase the conveying performance.

The mode of operation of a pump arrangement in accordance with the invention should be explained with reference to FIG. 2. The pump arrangement 10 includes a pump 11 which is formed as a rotor. The pump 11 is set into rotation by means of a shaft which is shown, but not numbered and can thus transport a driving flow $Q_T$. The pump arrangement 10 has a sheath 12 which includes a first section 12a and a second section 12b. An intake opening 13 is located in the first section 12a through which intake opening a fluid can enter into the lumen of the first section 12a, is sucked in by the pump 11 and is transported as a driving flow $Q_T$ in the direction of the outflow opening 14. The sheath 11 defines the flow passage S between the intake opening 13 and the outflow opening 14, said flow passage completely including the lumen of the first section 12a and partially including a lumen of the second section 12b.

The first section and the second section overlap between the proximal end of the first section 12a and the distal end of the second section 12b. An inlet opening 15 is defined by the overlap through which the fluid can enter into the flow passage S from a region outside the lumen of the first section 12a. A pressure drop occurs in the region 17 in the region of the proximal end of the first section 16 due to the driving flow $Q_T$ conveyed by the pump. This is shown in FIG. 3.

Further fluid is sucked through the inlet opening 15 in the direction of the outflow opening 14 due to the pressure drop in the region 17 and enters into the flow passage as the intake flow $Q_s$ proximal to the proximal end of the first section 16.

The first section 12a and the second section 12b both include a lumen. In this respect, the lumen of the first section 12a has a cross-sectional area $A_1$; the lumen of the second section 12b has a cross-sectional area $A_2$. In the present embodiment, the cross-sections $A_1$ and $A_2$ remain the same over the total length of the respective section; however, this is not a compulsory feature. The intake flow already receives an impulse direction in the direction of the outflow opening 14 due to the passage extending parallel to the driving flow between the distal end of the second section 12b and the proximal end of the first section 12a and formed as an inlet opening 15. The volume per time $Q_A$ which has flowed out at the outflow opening 14 is larger due to the additional intake flow $Q_S$ than the driving flow $Q_T$ passing through the pump.

A further embodiment of a pump arrangement is described in FIG. 4. The pump arrangement 20 is located in a blood vessel which is bounded by the vessel walls 4. The distal end of the pump arrangement 20 is located distal of the valve 5; the proximal end is located proximal to the valve 5.

The pump arrangement 20 includes a compressible rotor 21 which is fastened to the shaft 22 at one side. The bearing is located at the proximal end of the rotor. The rotor 21 is surrounded by a housing 23 which can be manufactured from Nitinol. The housing comprises individual threads, wires or struts of Nitinol which mutually cross and produce a diamond pattern. The fluid can pass through the diamonds and so reach the rotor 21.

The housing 23 is partly covered by a jacketing 24 in a fluid-tight manner. In this respect, the jacketing 24 extends over a length $L_{24}$ so that a driving flow $Q_T$ driven by the rotor is bundled and exits the housing 23 at the proximal end of the jacketing 24 and flows in the direction of the outflow openings 29 which are arranged in an outflow hose 25.

The jacketing 24 in the embodiment of the pump arrangement 20 forms the first section of the sheath; the outflow hose 25 forms the second section of the sheath. The distal end of the outflow hose is fastened to the housing 23 and is further distal than the proximal end of the sheath 24.

The sheath 34 converges from the region of the rotor 21 in the proximal direction. The lumen formed by the sheath 24 thus has a cross-sectional area $A_{1D}$ in the region of the rotor 21 which is larger than the cross-sectional area $A_{1P}$ of the proximal end of the sheath 24. A nozzle effect is hereby produced which accelerates the driving flow $Q_T$ in accordance with the principle of the Venturi tube so that it flows in the direction of the outflow openings 29 at a higher flow speed at the proximal end of the sheath 24. The intake passage 26 which is accessible through the inlets 27 is located between the sheath 24 and the outflow hose 25. It can be recognized from FIG. 4 that a plurality of inlets 27 are present, with the inlets being designed as circular sections of the outflow hose in the region of its distal end. Due to the reduced pressure in the region of the exiting driving flow $Q_T$ an intake flow $Q_s$ is sucked through the inlet 27 and the intake passage 26 and flows into the flow passage S, which transports the total conveyed flow to the outflow openings 29.

A support ring 28 which is stable in shape in the working state of the pump is located radially peripherally proximal to the inlets 27 and the outflow hose 25. A suction of the surface of the outflow hose 25 to the sheath 24 due to the occurring intake flow is thus prevented. The intake passage 26 thus remains open and further fluid is sucked through the intake passage 26, caused by the driving flow $Q_T$, into the flow passage S.

A further embodiment of the pump arrangement in accordance with the invention is shown in FIG. 5a. The pump arrangement 30 includes a rotor 31 which is supported at both sides, i.e. distal and proximal, at an axle 32. The rotor 31 is arranged in a housing 33 which is sectionally jacketed by a PU coating 34. The PU coating 34 in this respect extends over a length $L_{34}$ up to a region disposed proximal to the proximal end of the rotor 31. The housing 33 has a constriction 33a and expands proximal of the constriction 33a to form a bulge 33b. In the region of the bulge 33b, the outflow hose 35 is connected to the housing 33 with material continuity. The bulge 33b and the constriction 33a are spaced apart from one another, measured along the axis 32, by a spacing d which amounts to around 0 to ¼ of the diameter of the constriction 33a. In this respect, the spacing d is selected so that due to the driving flow $Q_T$ exiting the proximal end of the PU coating 34 and driven by the rotor 31, an intake flow $Q_s$ is sucked in through the inlet opening 36 resulting between the PU coating 34 and the outflow hose 35. The driving flow $Q_T$ exiting the jacketing is flowed out at a pressure $P_1$. A pressure $P_2$ applies outside the jacketing 34 which is lower than the pressure $P_1$. An intake flow $Q_s$ is sucked into the inlet opening 36 due to this pressure difference and is transported through the outflow hose toward the outflow opening 39 where it is expelled as a total current $Q_A$ at a pressure $P_3$ which is greater than the pressure $P_2$. The total flow $Q_A$ is in this respect lower than the driving flow $Q_T$.

Even if the flow passage S, which extends between the intake opening distal of the rotor 31 and the outflow opening 39, is permeable for fluid between the proximal end of the PU coating 34 and the distal end of the outflow hose 35, the inflow opening 36 nevertheless opens into the flow passage S which is defined by the flow course of the driving flow. If the driving flow is correspondingly high, it enters practically directly into the outflow hose.

It is possible due to the inlet opening present in addition to the intake opening disposed distal of the rotor 31 that a partial flow of the total flow $Q_A$ exiting at the outflow opening 39 does not pass the rotor 31 and there is thus no risk of blood damage by the rotor 31.

The embodiment of the pump arrangement 30 of FIG. 5a is shown again schematically in FIG. 5b. It can be recognized here that the distal end of the PU coating 34 has a cross-sectional area $A_{1D}$ which is larger with respect to the cross-sectional area $A_{1P}$ which is present at the proximal end of the PU coating 34. The lumen surrounded by the PU coating 34 thus converges, which has the consequence of an efficiency improvement. The cross-sectional area $A_{2D}$ of the lumen of the outflow hose 35 is in turn larger than the cross-sectional area $A_{1P}$. An inlet opening 36 is thus defined at least by the region of the cross-sectional area $A_{2D}$ which remains after the subtraction of the cross-sectional area $A_{1P}$. Said inlet opening in turn opens into the flow passage S.

A further embodiment of a pump arrangement is shown in FIG. 6. In this respect, a detailed description of the axle and of the pump drive is dispensed with. The pump arrangement 40 includes a rotor 41 as well as a first section 42a and a second section 42b of a sheath. The intake opening 43 which supplies fluid to the pump 41 is located at the distal end of the first section 42a. The fluid supplied to the pump 41 is accelerated and is expelled as a driving flow $Q_T$ at the proximal end of the first section 42a. The second section 42b is composed of a flexible region 420b which is connected to a compressible sleeve 421b which is of stable shape and is rigid in the working state of the rotor. The compressible sleeve 421b is connected to the first section 42a by means of plastic threads or wires 422b. The cross-section extending in converging manner from the distal end of the sleeve 421b to the proximal end of the sleeve 421b has the effect in conjunction with the driving flow $Q_T$ of sucking in an intake flow $Q_s$ through the inlet opening 45 which is formed between the sleeve 421b and the first section 42a, with the intake flow $Q_s$ being combined with the driving flow $Q_T$ and, in the flow passage S, flowing out of the outflow opening 44 as the total flow $Q_A$. It is in turn obvious from FIG. 6 that the inlet opening 45 opens into the flow passage S.

A further embodiment of a pump arrangement is shown in FIG. 7. The pump arrangement 50 includes a pump 51 which is formed as an axial-flow pump having a rotor. Furthermore, a sheath 52 is present which can be divided into a first section 52a and into a second section 52b. In this respect, the first section and the second section are connected to one another with material continuity or are manufactured in one piece. An intake opening 53, which supplies fluid to the rotor, is located at the distal end of the sheath 52 so that a driving flow $Q_T$ is conveyed in the working state of the rotor. The driving flow $Q_T$ is conveyed in the direction of the outflow opening 54. An inlet opening 55 through which an intake flow $Q_s$ effected by the driving flow $Q_T$ can enter into the flow passage S defined by the sheath 52 is located between the first section 52a and the second section 52b. The special feature of this embodiment is that the sheath 52 is made in one piece, in contrast to the previously shown embodiments in which the first section represents a separate component with respect to the second section.

Some different geometries of entries of the inlet openings should be shown with respect to FIGS. 8a-c.

A cross-section of the embodiment of FIG. 6 is shown in FIG. 8a. What can be seen is the intake opening 543 with a cross-sectional area $A_{1P}$. Disposed proximal thereto, i.e. further into the plane of the drawing, the sleeve 421b is located with the cross section $A_{2D}$ measured at its widest periphery. The plastic threads 422b connect the sleeve 421b to the first section 42a.

The embodiment of FIG. 5a is shown in FIG. 8b. The intake opening 33 can be recognized which is defined by the PU coating 34. The PU coating 34 simultaneously defines a lumen which has a cross-sectional area $A_{1D}$ in the region of the rotor. In addition, the axle 32 can be recognized at the center of the intake opening 33. Proximal to the rotor (cf. FIG. 5a), the housing 33 which is formed by threads, wires or struts of Nitinol converges to a cross-sectional area $A_{1P}$ which is defined by the constriction 33a. At proximal, the housing 33 widens to form a bulge 33b, with the outflow hose 35 being connected to the housing in the region of the bulge. It can clearly be recognized with reference to the representation shown in FIG. 8b that the region 36 disposed between the outflow whose 35 and the PU coating 34 serves as an inlet opening for an intake flow.

In FIG. 8c, the embodiment of FIG. 4 is shown. In this respect, the cross-section is shown at the level of the support ring 28. The lumen defined by the jacketing 24 of the first section and having the cross-sectional area $A_{1D}$ can be recognized. The intake passage 26 through which additional fluid is sucked in, driven by the driving flow running through the lumen of the jacketing 24 in the proximal direction, is located between the jacketing 24 and the outflow hose 25. The outflow hose 25 has a cross-sectional area of $A_{2D}$ in this region. The support ring 28 can clearly be recognized, as can the connection struts 28a which connect the support ring to the jacketing 24. The support ring is composed of a plurality of segments 28b which can be brought into a folded state for introduction of the pump arrangement with the aid of a catheter.

REFERENCE NUMERAL LIST 1, 10, 20, 30, 40, 50 pump arrangement
2 blood vessel
3 ventricle
4 vessel wall 5 heart valve
6 vessel valve
11, 41, 51 pump
12, 42, 52 sheath
12a, 42a, 52a 1st section of the sheath
12b, 42b, 52b 2nd section of the sheath
13, 43, 53 intake opening
14, 44, 54 outflow opening
15 inlet opening
16 proximal end of the 1st section
17 region of pressure drop
21, 31 rotor
22, 32 axle
23, 33 housing
24, 34 jacketing
L24,-L34 length of the jacketing
25, 35, 420b outflow hose
26, 36 intake passage
27 inlets
28 support ring/spacer
33a constriction
33b bulge
421b sleeve
422b spacer
$Q_T$ conveyed flow
$Q_s$ intake flow
$Q_A$ total flow
$A_1, A_2, A_{1D}, A_{1P}, A_{2D}$ cross-section

The invention claimed is:

1. A blood pump assembly comprising:
an elongate catheter having a proximal end and a distal end;
a compressible rotor disposed at a distal end of the elongate catheter;
a housing surrounding the compressible rotor, the housing including a proximal end and a distal end, the housing shaped to define a flow-path and comprising:
a first fluid-tight section disposed at the distal end of the housing, the first fluid-tight section comprising a distal end defining a distal opening, a proximal end defining a proximal opening, and a central bore extending from the distal opening to the proximal opening, the central bore being radially fluid tight between the distal opening and the proximal opening;
a second fluid-tight section at least partially comprised of an elastic material and disposed at the proximal end of the housing, the second fluid-tight section comprising a flared distal end, a first blood inlet disposed at a distal end of the second fluid-tight section, and a blood outlet disposed at a proximal end of the second fluid-tight section, wherein the flared distal end defines the first blood inlet, and wherein the second fluid-tight section is radially fluid-tight between the first blood inlet and the blood outlet;
wherein the second fluid-tight section and the first fluid-tight section are coaxial, wherein a cross-sectional area of a proximal end of the first fluid-tight section is smaller than a cross-sectional area of a distal end of the second fluid-tight section, and wherein the proximal end of the first fluid-tight section is distal to a proximal end of the second fluid-tight section.

2. The blood pump assembly of claim 1, wherein the portion of the second fluid-tight section comprised of a flexible material is elastically compressible.

3. The blood pump assembly of claim 2, wherein first fluid-tight section is coupled to the second fluid-tight section by one or more wires.

4. The blood pump assembly of claim 3, wherein the housing comprises nitinol struts.

5. The blood pump assembly of claim 4, wherein the distal opening of the second fluid-tight section defines a second blood inlet.

6. The blood pump assembly of claim 5, wherein the second blood inlet has a circular cross-section.

7. The blood pump assembly of claim 6, wherein the first blood inlet and the second blood inlet are coaxial.

8. The blood pump assembly of claim 7, wherein the cross-sectional area of the central bore of the first fluid-tight section is substantially constant.

9. The blood pump assembly of claim 8, wherein the first fluid-tight section further comprises a bulge.

10. The blood pump assembly of claim 9, wherein the bulge is disposed distal to a constriction of the first fluid-tight section.

11. The blood pump assembly of claim 10, wherein the elongate catheter is sized for percutaneous insertion into a blood vessel of a patient.

12. The blood pump assembly of claim 11, wherein the rotor is disposed within the first fluid-tight section.

13. The blood pump assembly of claim 1, wherein the flared distal end of the second fluid-tight section at least partially encloses the first fluid-tight section.

14. A blood pump assembly comprising:
an elongate catheter having a proximal end and a distal end;
a compressible rotor disposed at a distal end of the elongate catheter;
a housing surrounding the compressible rotor, the housing including a proximal end and a distal end, the housing shaped to define a flow-path and comprising:
a first fluid-tight section disposed at the distal end of the housing, the first fluid-tight section comprising a distal end defining a distal opening, a proximal end defining a proximal opening, and a central bore extending from the distal opening to the proximal opening, the central bore being radially fluid tight between the distal opening and the proximal opening, wherein the central bore has a circular cross section;
a second fluid-tight section at least partially comprised of an elastic material and disposed at the proximal end of the housing, the second fluid-tight section comprising a flared distal end, a first blood inlet disposed at a distal end of the second fluid-tight section, and a blood outlet disposed at the proximal end of the second fluid-tight section, wherein the flared distal end defines the first blood inlet, wherein the second fluid-tight section is radially fluid tight between the first blood inlet and the blood outlet;
wherein the second fluid-tight section and the first fluid-tight section are coaxial, wherein a cross-sectional area of a proximal end of the first fluid-tight section is smaller than a cross-sectional area of a distal end of the second fluid-tight section, wherein the proximal end of the first fluid-tight section is distal to a proximal end of the second fluid-tight section, and wherein the second fluid-tight section is coupled to the first fluid-tight section by one or more wires.

15. The blood pump assembly of claim 14, wherein the first fluid-tight section further comprises a bulge.

16. The blood pump assembly of claim 15, wherein the bulge is disposed distal to a constriction of the first fluid-tight section.

17. The blood pump assembly of claim 16, wherein the housing comprises nitinol struts which form a diamond pattern.

18. The blood pump assembly of claim 17, wherein the elongate catheter is sized for percutaneous insertion into a blood vessel of a patient.

19. The blood pump assembly of claim 18, wherein the rotor is disposed within the first fluid-tight section.

20. The blood pump assembly of claim 14, wherein the flared distal end of the second fluid-tight section at least partially encloses the first fluid-tight section.

* * * * *